United States Patent [19]
Usui

[11] Patent Number: 5,879,378
[45] Date of Patent: *Mar. 9, 1999

[54] EXOTHERMIC DEVICE AND AN APPLICATION PAD USING THE SAME

[75] Inventor: Akio Usui, Tochigi, Japan

[73] Assignee: Kabushiki Kaisha Genchi Kenkyusho, Tochigi Pref., Japan

[*] Notice: This patent issued on a continued prosecution application filed under 37 CFR 1.53(d), and is subject to the twenty year patent term provisions of 35 U.S.C. 154(a)(2).

[21] Appl. No.: 592,955

[22] Filed: Jan. 29, 1996

[30] Foreign Application Priority Data

Feb. 6, 1995 [JP] Japan .................................. 7-042348

[51] Int. Cl.$^6$ ........................................ A61F 7/00
[52] U.S. Cl. .............. 607/96; 607/108; 604/20; 604/113; 126/263.07; 126/263.02
[58] Field of Search .................... 602/2; 604/289, 604/291, 304, 307, 113, 20; 607/96, 104, 108, 112, 114; 126/263.01, 263.02, 263.05–263.07, 204

[56] References Cited

U.S. PATENT DOCUMENTS

| | | | |
|---|---|---|---|
| 4,205,685 | 6/1980 | Yashida et al. | 607/96 |
| 4,925,743 | 5/1990 | Ikeda et al. | 607/114 |
| 5,233,981 | 8/1993 | Miyashita | 126/263.01 |
| 5,366,492 | 11/1994 | Ueki | 607/114 |

*Primary Examiner*—Mark Bockelman
*Attorney, Agent, or Firm*—Edwin E. Greigg; Ronald E. Greigg

[57] ABSTRACT

An exothermic device has an exothermic composition enclosed in a flat pouch formed of film or sheet, at least one surface thereof being gas-permeable. The exothermic composition comprises a laminate of an exothermic reaction layer having an exothermic substance as an essential ingredient thereof, and a single or a plurality of reaction auxiliary layer(s) including other ingredients. The exothermic device is incorporated into a sticking pad applicable to the human body to provide a warming and/or therapeutic effect.

32 Claims, 3 Drawing Sheets

EXOTHERMIC DEVICE AND AN APPLICATION PAD USING THE SAME

BACKGROUND OF THE INVENTION (1) Field of the Invention

The present invention relates to an exothermic device and an application pad using the same, and more particularly to an exothermic device and a pad using the same, which are capable of eliminating various harmful effects due to an exothermic reaction or coagulation of an exothermic composition occurring in time of manufacture, in particular, which are ultra-thin, have a uniform thickness, and are soft and readily conformable to any curved areas of the human body or the like, which readily follow expansions and contractions of a surface of the human body or the like, and which are free from movement of the exothermic composition during use to give a comfortable feel to the wearer.

(2) Description of the Related Art

In recent years, exothermic devices each having an exothermic composition enclosed between two films or sheets at least one of which is gas-permeable have become widespread as warming devices called disposable body warmers. Some exothermic devices forming the disposable body warmers have an adhesive layer formed on one surface thereof to be applied to the human body or the like. The exothermic devices with a warming effect are increasingly used as applied pads to promote metabolism such as blood circulation or to facilitate absorption of skin absorbable medicine (see Patent Laying-Open Publication No. 2-149272).

Most of the conventional exothermic devices are manufactured by a method based on a technical concept of enclosing an exothermic composition, which generates heat through a reaction with oxygen in the air, in a flat gas-permeable pouch, so that the exothermic composition may be applied directly or through clothing such as underwear to a surface of the human body or the like.

Specifically, according to this manufacturing method, the exothermic composition is injected to fill into a flat inner pouch formed of films or sheets at least one of which is gas-permeable, with three sides closed and one side open, and then the open side is sealed. Alternatively, the exothermic composition is placed on a gas-permeable film or sheet, and then the film or sheet is formed into a pouch with three sides sealed or four sides sealed. The pouch is thereafter inserted into a gastight outer pouch.

The exothermic composition is prepared by mixing a metal powder acting as an exothermic substance, a carbon-containing substance such as carbon powder acting as an exothermic promoter, a chloride and water acting as a reaction promoter (reducing agent), and a water retainer to prevent stickiness. In a traditional manufacturing method, all of these ingredients are blended and then filled into a pouch or placed on a film or sheet which is subsequently formed into a pouch.

As these ingredients are blended in air, an exothermic reaction of the exothermic composition with the oxygen in air is started when all of the ingredients thereof have been blended, and the coagulation of the composition will be started and proceeded in the process of the exothermic reaction.

This gives rise to the problem that, after preparation of the exothermic composition and before insertion thereof into the outer pouch, heat is generated to constitute a heat loss which is not utilized by a wearer of the exothermic device, resulting in a lowering of quality.

A filling apparatus for filling the exothermic composition into the pouch, or a feeding apparatus for feeding the exothermic composition onto a film or sheet, includes a hopper for storing the exothermic composition, and a chute connected to a lower position of the hopper. The exothermic composition of a predetermined quantity is injected into every pouch, or intermittently on a film or sheet running at a speed in the atmosphere.

When the quantity of the exothermic composition in the hopper is decreased below a predetermined quantity, a preferable amount of the exothermic composition blended by a mixer beforehand is replenished, or ingredients of the composition are replenished in the hopper and blended therein.

It is therefore very difficult to maintain the interior of such apparatus shielded from the atmosphere. The exothermic composition may undergo an exothermic reaction or coagulation inside the hopper or chute of the apparatus, often disrupting manufacture or causing quality variations.

Furthermore, before a noon recess and closing of work for the day, the filling apparatus or feeding apparatus must be stopped after the exothermic composition has been exhausted therefrom in order to avoid coagulation of the exothermic composition in the apparatus. Besides, it is necessary to carry out operations, after the exothermic composition is exhausted from the apparatus, to seal the filling apparatus or feeding apparatus and to remove any reaction product adhering to the filling apparatus or feeding apparatus.

The operation for removing the reaction product operation must deal with dust adhering to and remaining on the walls inside the hopper and chute. Thus, the operation is an irksome and ugly operation involving scraping with knives and cleaning with water.

Moreover, if such a removal operation was not carried out before a noon recess or after closing of work, the exothermic composition is maintained in a sealed condition in the filling apparatus or feeding apparatus till commencement of work in the following day, but the exothermic composition solidifies under gravity or undergoes a reaction through contact with air or the like inside the hopper. As a result, the exothermic composition partly coagulates, thereby to bring about variations in the feed and fluidity of the exothermic composition.

Incidentally, sealing of the hopper ordinarily is not more than closing the hopper with a lid. Some air will enter through gaps around the lid to cause coagulation of the exothermic composition. Consequently, clogging of the filling chute or feeding chute is encountered repeatedly, almost every morning.

In addition, the exothermic composition cannot be stored in the filling apparatus or feeding apparatus over a long period of production downtime occurring with introduction of a five-day week or at the year-end to new year holiday, summer holiday, or other consecutive holidays. It is therefore necessary to dispense the exothermic composition in the filling apparatus or feeding apparatus or thoroughly remove it by washing or cleaning. Moreover, the exothermic composition removed from the apparatus by washing or cleaning has already undergone a change in composition and ingredient. Such exothermic composition is not preferable to reuse and must be discarded, thereby resulting in a low yield. Besides, as it is distinct from ordinary wastes, this waste must be treated as so-called industrial waste which involves a high cost of treatment.

Furthermore, a mixer for mixing the ingredients of the exothermic composition tends to be wet with moisture in the compound. Thus, the ingredients of the compound tend to adhere thereto and tend to coagulate through the reaction. It is therefore necessary to carry out an irksome and ugly operation after closing of work every day, which includes scraping with knives and cleaning with water. A considerable amount of adhering matter must be discarded as industrial waste.

Besides, the manufacturing apparatus must have mounted therein a device for preventing bridging of the exothermic composition. Thus, the apparatus is complicated and expensive. There is a further disadvantage that, with filling or feeding of the exothermic composition, dust scatters to the ambient to pollute the working environment.

In the conventional method in particular, the exothermic composition is injected into a flat inner pouch formed of films or sheets at least one of which is gas-permeable, with three sides closed and one side open, and then the open side is sealed. Alternatively, the exothermic composition is scattered on a gas-permeable film or sheet, and then the film or sheet is formed into a pouch. Since, with this method, the exothermic composition having a water content is injected into or scattered on the gas-permeable film or sheet, it is difficult to secure a uniform thickness, which results in serious problems such as variations in temperature distribution.

Besides, it is difficult with the conventional method to form the water-containing exothermic composition injected into or scattered on the gas-permeable film or sheet, to be thin below a predetermined value of thickness. That is, the exothermic composition is formed thick so that it has difficulties in conforming to a complicated curve of a body surface or a curved surface of small curvature and in following expansions and contractions and changes in the shape of a body surface. It also gives a stiff feel.

In addition, since, with this method, the exothermic composition having a water content is injected into or scattered on the gas-permeable film or sheet, not only the exothermic composition is easy to move within the pouch, but the exothermic device is made thick and the exothermic composition tends to move within the pouch. Consequently, the exothermic composition in the pouch tends to be moved during use or during transport.

Incidentally, an ultra-thin, soft, sheet-like exothermic device with ease of temperature control is desired to be made available in the medical field in the future.

There is a strong demand especially for an exothermic sheet formed as ultra-thin as possible to be used as an exothermic device for skin absorption of medicine. With the conventional exothermic composition having all ingredients mixed together, the powdery mixture becomes granulated to form an unsmooth exothermic device. The resulting disadvantages are not only poor adhesion to the skin, but variations in the exothermic composition per se which result in variations in temperature distribution.

Conventionally, a movement of the exothermic composition is prevented by controlling gas-permeability of a porous film to decompress the interior of the covering. However, since the exothermic device per se is thick and the exothermic composition tends to move as noted above, the exothermic composition may be moved in the presence of pinholes in the covering or pinholes formed in time of heat sealing. Just before the end of a exothermic action, the degree of decompression in the covering is lowered, i.e. the covering interior approaches atmospheric pressure, whereby the exothermic composition moves to one side within the covering. A maldistribution occurs also when the heat of the exothermic device exceeds a fixed temperature.

Further, the exothermic composition becomes compact and hard since the interior of the covering is decompressed during use of the exothermic device. Consequently, when it was applied directly to the skin, it gives an unsmooth feel and causes trouble due to skin stress.

SUMMARY OF THE INVENTION

The present invention has been completed having regard to the technical subject matter noted above, and its object is to provide an exothermic device and an application pad using the same, which are capable of eliminating various harmful effects due to an exothermic reaction or coagulation of an exothermic composition occurring in time of manufacture in particular, which are ultra-thin, have a uniform thickness, and are soft and readily conformable to any curved areas of the human body or the like, which readily follow expansions and contractions of a surface of the human body or the like, and which are free from displacement of the exothermic composition during use to give a comfortable feel to the wearer.

[Description of the Exothermic Device of the Present Invention]

The exothermic device according to the present invention has an exothermic composition comprising an exothermic substance and at least one other ingredient enclosed in a flat gas-permiable pouch of a film or sheet. The exothermic substance is stable in air per se, activated to react with the oxygen in the air by the other ingredients and to generate heat. And each one of the other ingredients is stable in air per se, and activates the exothermic substance to perform an exothermic reaction with oxygen in air when all of these is mixed together with the exothermic substance in an appropriate proportion.

The most significant character of the invention is that the exothermic composition is formed in layers comprising at least one exothermic reaction layer coated on a film or sheet and at least one reaction auxiliary layer coated on and/or under the exothermic reaction layer on the film or sheet.

The exothermic reaction layer includes an exothermic substance as an essential ingredient thereof. That is, the exothermic reaction layer is composed of an exothermic substance solely, or of a mixture comprising an exothermic substance and at least some of the other ingredients of the exothermic composition, being arranged to not start an exothermic reaction in air. And the reaction auxiliary layer comprises at least one of the other ingredients of the exothermic composition except the exothermic substance.

The present invention will be described in detail hereinafter.

(Description of the Pouch)

The pouch used in the present invention is not limited to any particular type as long as it has a necessary mechanical strength such as tensile strength and has at least one surface thereof formed of a gas-permeable flat film or sheet. However, it should be preferably soft and conformable to uneven parts body surface or clothing. Where the exothermic device is used for a medical application pad, it should have preferably elasticity in directions along its plane to be capable of following movements of a body surface or clothing to which it is applied.

The pouch used in the present invention must have at least one surface thereof formed of a gas-permeable film or sheet in order to allow the exothermic composition enclosed in the pouch to contact with oxygen in the atmosphere. The pouch may be formed by doubling or tripling a single gas-permeable film or sheet. The pouch may be formed by placing, a single gas-permeable film or sheet and a single gas-tight film or sheet one over the other and joining them by heat sealing or with a hot melt type adhesive. The pouch may be formed by placing, two gas-permeable films or sheets one over the other and joining them by heat sealing or with a hot melt type adhesive.

However, where the pouch is formed by doubling or tripling a single gas-permeable film or sheet, it is necessary to fold the film or sheet after the layers comprising at least one exothermic reaction layer and at least one a reaction auxiliary layer are formed thereon as described later. Where two films or sheets are placed one over the other, it is necessary to join the two films or sheets after the layers comprising at least one exothermic reaction layer and at least one reaction auxiliary layer are formed on one of the films or sheets as described later.

The film or sheet for forming the pouch is not limited to any particular material. Usable materials include, for example, polymeric materials such as polyethylene, polypropylene, polyamide, polyester, polyvinyl chloride, polyvinylidene chloride, polyurethane, polystyrene, saponified ethylene-vinyle acetate copolymer and ethylene-vinyle acetate copolymer; paper; cloths and the like.

The usable cloths include a nonwoven fabric and woven fabric of natural fiber, synthetic fiber and a mixture thereof. It is of course possible to use films of the above polymeric materials, paper, woven fabric, unwoven fabric, foamed gas-permeable films or sheets of the above polymeric materials (hereinafter referred to as foam sheets), and a laminate of two or more of the above materials.

Recommendable one among these materials to realize mechanical strength, elasticity and softness in harmony is a laminate of paper, fabric or foam sheet and a non-foam, gas-permeable film of a polymeric material. It is particularly preferable to use a laminate film or laminate sheet of nonwoven fabric and a gas-permeable film of a polymeric material.

As a laminate film or laminate sheet on which the exothermic composition is formed before the laminate films or laminate sheets at the opposite surfaces are joined, it is recommendable to use a film or sheet having a two-layer structure with paper, fabric or foam sheet disposed inwardly of the pouch and a gas-permeable film of a polymeric material disposed outwardly, in order to facilitate lamination of the exothermic composition and to enhance bonding strength with respect to the exothermic composition.

Further, as a laminate film or laminate sheet to be laminated on the laminate film or laminate sheet on which the exothermic composition has been laminated, it is recommendable to use a film or sheet having a three-layer structure with paper, woven fabric, nonwoven fabric or foam sheet disposed inwardly of the pouch, woven fabric, nonwoven fabric or foam sheet disposed outwardly, and a gas-permeable film of a polymeric material sandwiched between these two layers, in order to enhance feel.

Where the gas-permeable film or sheet is applied after the exothermic composition is laminated on a different film or sheet as described later, movement of the exothermic composition inside the pouch is effectively prevented by bonding with the different film or sheet. Therefore, the paper, fabric or foam sheet laminated inwardly may be omitted, and only the gas-permeable film or sheet of a polymeric material may be used. Alternatively, it is possible to use a film or sheet of two-layer structure with the gas-permeable film or sheet of a polymeric material disposed inwardly of the pouch, and paper, woven fabric, nonwoven fabric or foam sheet disposed outwardly of the pouch.

Typical examples of the gas-permeable film or sheet of a polymeric material include a porous film or sheet formed by a drawing process, extraction of particular ingredients, foaming or the like, and a perforated film or sheet with bores formed by a mechanical process such as punching or boring.

Incidentally, it is the most desirable that the flat pouch used in the present invention is formed by laminating a thermally fusible nonwoven fabric on a gas-tight film or sheet, laminating a reaction auxiliary layer on the thermally fusible nonwoven fabric, laminating an exothermic reaction layer thereon, and superposing a gas-permeable film or sheet further thereon, so that peripheries thereof are thermally fusible.

Where seal portions of the pouch are sealed by heat sealing, a film or sheet for forming the seal may be a gas-permeable film or sheet as is the gas-permeable surface. However, it is preferable to use a gas-tight film or sheet to diminish loss due to moisture permeation.

Further, the film or sheet applicable to a surface should preferably be elastic to enhance conformability to the surface to which it is applied. Further, it should preferably be non-stimulative to the human skin to avoid an allergic inflammation.

Where a gas-tight film or sheet of a polymeric material is used for the application surface of the pouch, the material of this film or sheet is not limited. Polymeric materials usable include, for example, polyethylene, polypropylene, polyamide, polyester, polyvinyl chloride, polyvinylidene chloride, polyurethane, polystyrene, saponified ethylene-vinyle acetate copolymer and ethylene-vinyle acetate copolymer.

The film or sheet for forming the application surface may be a laminate of a film or sheet of a gas-tight polymeric material as noted above, and paper, woven fabric, nonwoven fabric or foam sheet or two or more of these materials.

Among these materials, a laminate of paper, woven fabric, nonwoven fabric or foam sheet and a gas-tight film of a polymeric material is preferable in order to realize mechanical strength, elasticity and softness in harmony.

In the present invention, paper, woven fabric, nonwoven fabric or foam sheet used adjacent the exothermic reaction layer or reaction auxiliary layer should preferably be thermally fusible in order to facilitate manufacture of the exothermic device by heat sealing.

Where the exothermic composition is laminated on the film or sheet forming the application surface, it is recommendable to use a film or sheet having a two-layer structure with paper, woven fabric, nonwoven fabric or foam sheet disposed inwardly of the pouch and a gas-tight film of a polymeric material disposed outwardly, in order to facilitate lamination of the exothermic composition and to enhance bonding strength between the exothermic composition and the film or sheet to prevent movement of the exothermic composition inside the pouch.

However, where the gas-tight film or sheet is applied after the exothermic composition is laminated on the gas-permeable film or sheet at one surface, movement of the exothermic composition inside the pouch is effectively prevented by bonding with the gas-permeable film or sheet at one surface. Therefore, only a single gas-tight film or sheet of a polymeric material may be used.

The above pouch is not limited to have a particular shape. Specifically, it may be polygonal such as triangular, square, rectangular, pentagonal or hexagonal, or circular, elliptic, star-shaped or gourd-shaped, for example. Further, it may be X-shaped, Y-shaped, or may have any desired shape, for example, with appropriate cutouts formed in peripheries of the pouch having any of the above shapes to be conformable to a particular site of the human body. Of course, there is no limitation in size, either.

The above pouch may be a single-chamber pouch or a multi-chamber pouch having a plurality of chambers. The exothermic device may readily be made conformable to a curved surface by forming partitions between the chambers of the multi-chamber pouch or by forming a chamber or chambers with one or more layers of the exothermic composition. The exothermic device may be made still more conformable to a curved surface where the film, sheet or fabric forming one continuous surface and/or opposite surfaces is elastic.

The film or sheet for forming the pouch is not limited to any particular thickness, but preferably is in the order of 5 $\mu$m to 1 mm. With a film thickness less than 5 $\mu$m, it is difficult to obtain a uniform thickness, and is not desirable since necessary mechanical strength may not be provided. On the other hand, a film thickness exceeding 1 mm is undesirable in that it lowers the conformability to a body surface and the ability to follow variations of the body surface, and may impair feel. An optimal result is obtained from a film or sheet thickness in the range of 15 to 250 $\mu$m. The film or sheet may have the same thickness or different thicknesses at the front and back of the pouch.

In the pouch used in the present invention, the film or sheet at the side to contact with the human skin, preferably, has an ability to absorb a secretion such as sweat or a body fluid from a wound, or water absorbing capability.

Specific examples include a gas-permeable film or sheet with a water retainer sprayed or coated on an inner surface thereof, a gas-permeable film or sheet with water-absorptive paper, woven fabric, nonwoven fabric or foam sheet laminated on an inner surface thereof, and a gas-permeable film or sheet with paper, woven fabric, nonwoven fabric or foam sheet carrying a water retainer such as a water-absorptive polymer and laminated on an inner surface thereof.

(Description of the Exothermic Composition)

Next, the exothermic composition is not limited as long as it brings about an exothermic reaction in the presence of air, whether it is an organic substance, an inorganic substance or a mixture thereof.

Specifically, a known exothermic composition (so-called chemical heater) may be used, which includes, for example, a metal powder acting as an exothermic substance, carbon powder having an action to cause oxidation of the metal powder and PH adjusting and catalytic actions, a metallic chloride for breaking oxide film on surfaces of the metal powder to promote smooth oxidation of the metal powder, water, a water retainer for avoiding sogginess due to the water, an inhibitor against film formation due to dryness, a surface active agent for improving dispersion, and an antifoaming agent.

The metal powder may be iron powder, zinc powder, aluminum powder, magnesium powder, or powder of an alloy of two or more of these substances. However, iron powder is the most desirable from the point of view of safety, handling convenience, cost, storage characteristics, stability, and so on.

Carbon powder may comprise activated carbon, carbon black or graphite. For use in the form of mucus, it is desirable to provide a fine powder of 200 mesh or less.

In a preferred known exothermic composition, particularly from the point of view of stability, economy, continuance of heating effect and storage characteristics, metal powder is used as the exothermic substance, and ingredients of the exothermic composition in the exothermic device are in the following proportions: 40 to 80% by weight of a metal powder, 1 to 20% by weight of carbon powder, 0.5 to 5% by weight of a metallic chloride, 5 to 40% by weight of water, and 1 to 10% by weight of a water retainer.

The metallic chloride may be a chloride of an alkali metal such as sodium chloride or potassium chloride, or a chloride of an alkali earth metal such as calcium chloride or magnesium chloride.

(Description of Lamination of the Exothermic Composition)

It is particularly important that the present invention is characterized in that the exothermic composition is formed in layer comprising an exothermic reaction layer having an exothermic substance as an essential ingredient thereof, printed on the film or sheet by way of transfer, screen printing or gravure, and at least one of reaction auxiliary layer(s) including other ingredients printed on and/or under the exothermic reaction layer on the film or sheet.

For example, in the present invention, a plurality of exothermic layers in which proportions are different from that of each other may be formed to arrange a total of proportions of the exothermic reaction layer or that of an exothermic composition. It is also possible to print a plurality of exothermic layers of the same proportion for several layers to obtain a predetermined thickness of the exothermic reaction layer or that of the exothermic composition. The same things are applied to the reaction auxiliary layer. It must be regarded that every layer is stable in air per se, and separated from the other layer before it will be printed on or under the other layer, and that these layers are enclosed in a pouch as soon as all of their printing on a film or sheet is finished. Thus, no exothermic reaction of the exothermic composition with oxygen in air is made before it is enclosed in the pouch. Thus, no exothermic reaction occurs even through a contact with air is made before it is enclosed. As described in detail later, this eliminates various disadvantages due to an exothermic reaction or coagulation of the exothermic composition occurring in time of manufacture, and allows the exothermic composition to be formed thin, thereby rendering the entire exothermic device thin. Consequently, improvement has been made in conformability to any curved surface of the human body or the like and the ability to follow variations of the body surface, and in the feel to the user.

In order to avoid the exothermic reaction before the exothermic composition is enclosed in a gas-tight pouch, it is preferable to make an exothermic reaction layer of exothermic substance, such as metal powder, alone. However, at least one of the ingredients other than the exothermic substance may be included in an exothermic reaction layer unless it will arise a substantial exothermic reaction in air after it has been mixed with the exothermic substance before the exothermic composition will be enclosed in a gas-tight pouch.

In the present invention, the exothermic composition is formed of at least two layers comprising at least one exothermic layer and at least one reaction auxiliary layer. And at least one of the layers is preferable to be liquid or mucous in order to avoid the polluting the circumference by the ingredients and to make the dispersion of the ingredients into the exothermic layer easy.

A liquid layer is made of water alone or an aqueous solution of metallic chloride, and a mucous layer is made of liquid, such as water or an aqueous solution of metallic chloride, and at least one of powdered ingredients such as an exothermic substance, carbon powder, and a water retainer of course, a layer except liquid or mucous one is made of at least one of the powdered ingredients, such as an exothermic substance, carbon powder, a water retainer and a metallic chloride.

For example, where the exothermic composition is formed in two layers, one of them is made of a powdered exothermic reaction layer for enhancing the efficiency of contact with air, and the other one is a mucous reaction auxiliary layer.

In this example, the powdered exothermic reaction layer is preferably made of metal powder, and the all of the other ingredients is preferably included in the mucous reaction auxiliary layer. However, in this example, one or some of the powdered ingredients other than exothermic substance may be included in the exothermic reaction layer, unless it will arise a substantial exothermic reaction in air.

In a different example, where the exothermic composition is formed in two layers, one of them is a powdered exothermic reaction layer and the other one is a liquid reaction auxiliary layer.

In this example, the liquid reaction auxiliary layer includes water or an aqueous solution of metallic chloride, and all of the other powdered ingredients, i.e., metal powder, carbon powder, a water retainer, and possibly a metallic chloride, are included in the exothermic reaction layer.

Where the exothermic composition is formed in three layers, one of them is a powdered exothermic layer, one of the others is a powdered reaction auxiliary layer, and the other is a liquid or mucous reaction auxiliary layer, for example.

In this example, the powdered exothermic reaction layer may be made of metal powder alone, the powdered reaction auxiliary layer may be made of one of the powdered ingredients except the exothermic substance, such as carbon powder, a water retainer, or a metallic chloride, and the mucous reaction auxiliary layer is a mixture of a liquid such as water or an aqueous solution of metallic chloride, carbon powder and/or a water retainer.

However, in this case, the powdered reaction auxiliary layer may be a mixture of carbon powder, a water retainer and/or possibly a metallic chloride.

In this example, the powdered exothermic reaction layer may be a mixture of metal powder and at least one of the others may be powdered ingredients, such as carbon powder, a water retainer, and a metallic chloride. That is, the powdered exothermic reaction layer may be a mixture of metal powder and carbon powder, a mixture of metal powder and a water retainer, a mixture of metal powder, carbon powder and a water retainer, a mixture of metal powder, carbon powder and a metallic chloride, a mixture of metal powder, a water retainer and a metallic chloride, or a mixture of metal powder, carbon powder, a water retainer and a metallic chloride.

In the present invention, the powdered ingredients except an exothermic substance, such as carbon powder, a water retainer, and a metallic chloride, can be divided into a plurality of parts and used in a plurality of layers. For example, a water retainer may be divided in three parts and mixed in a powdered exothermic reaction layer, a powdered reaction auxiliary layer, and a mucous reaction auxiliary layer.

Where the powdered ingredient, such as a water retainer, is used in a plurality of layers, the substance of the ingredient in each layer may be the same with or different from that of the other.

The proportion of the ingredients such as a water retainer in each layer is determined taking account of productivity of the exothermic composition, viscosity of the layer, easiness of printing, and so on.

The exothermic composition may be formed in three layers, including two exothermic reaction layers and a reaction auxiliary layer made between the exothermic layers.

Further, according to the present invention, the exothermic composition is formed in more than four layers, including at least two exothermic reaction layers and at least two reaction auxiliary layers.

In this case, the exothermic reaction layers and the reaction auxiliary layers are advantageously made alternatively.

For example, in case that the exothermic composition is formed in four layers, a reaction auxiliary layer and an exothermic reaction layer may be laminated on a gas-permeable film or sheet in the order, and an other reaction auxiliary layer and an other exothermic reaction layer laminated on a gas-tight film or sheet in the order. The exothermic reaction layers are placed in contact with each other, and the films or sheets are thermally fused at their peripheries.

Alternatively, a reaction auxiliary layer, an exothermic reaction layer, an exothermic reaction layer and a reaction auxiliary layer may be laminated successively on a gas-permeable film or sheet, then a gas-tight film or sheet may be placed thereon, and peripheries of films or sheets may be thermally fused.

In the present invention, compositions of the exothermic reaction layer and reaction auxiliary layer are determined with a view to facilitate manufacture and prevention of dust scattering to the circumference.

Specifically, for example, it is preferred that a sequence of forming a layer of mucous or a layer of liquid, and laying a layer of powder on the layer of mucous or layer of liquid is repeated a necessary number times to form layers of mucous or layers of liquid and layers of powder alternately.

In this case, the layer of slime or liquid does not necessarily mean a uniform layer of slime or liquid, but means a state in which moisture is given to an application surface of the layer. Whether an inward penetration takes place after application is not questioned.

In the present invention, where a layer of liquid is provided, a layer of slime with a water retainer added thereto is preferred in order to prevent adhesion to the ambient during manufacture, to facilitate formation of the exothermic reaction layer and reaction auxiliary layer into a predetermined pattern, and to avoid leakage of the liquid into the ambient or rendering the ambient sticky when a hole is formed in a sealed pouch or when the sealed pouch is torn.

The water retainer used in the present invention is not limited as long as it is soluble or dispersible in water or an aqueous solution of a metallic chloride to hold water or to increase viscosity of water or the aqueous solution of a metallic chloride. Specifically, what are usable are, for example, starch water retainers, polysaccharide water retainers, cellulose derivative water retainers, acrylic resin water retainers, polyvinyl alcohol water retainers, urea resin water retainers and dispersed emulsion water retainers.

The starch water retainers may comprise dextrin, alphatized starch, and starch for processing, for example.

Typical examples of the polysaccharide water retainer are sodium alginate and agar. Examples of the cellulose derivative water retainer include carboxyl methyl cellulose (CMC), ethyl acetate cellulose, and hydroxypropyl cellulose. Typical examples of the dispersed emulsion water retainer are polyvinyl acetate emulsion, and polybutadiene emulsion. Other usable water retainers include acrylate soda, and adhesives.

A preferred water retainer is highly soluble or dispersible, has no unpleasant smell, is stable and does not putrefy easily.

Further, the water retainer preferably facilitates control and handling of materials in the manufacturing process, is not toxic and is highly soluble.

A compounding ratio for the water retainer is determined, taking into account the ratio of the ingredients of the foregoing exothermic composition, and the questions on printing such as patterning of the layer, transferability in transfer, precision in screen printing, depth of plate, and so on.

Forming of the exothermic reaction layer and reaction auxiliary layer may be done successively from one surface, and is not limited to any particular mode. The first layer formed on a film or sheet directly may be powdered one, liquid one, or mucous one, but is preferred to be caought effectively by the film or sheet in order to prevent scattering or movement of the exothermic composition in the pouch and to maintain a uniform distribution of components in the pouch. In forming the layer of mucous or liquid, the film or sheet used should preferably be water absorptive.

Specifically, a preferred sequence of lamination is such that, for example, a reaction auxiliary layer comprising a layer of mucous or liquid is printed onto a gas-permeable or gas-tight film or sheet at one surface, the pattern of the layer is formed within a predetermined transfer region by screen printing, gravure with a released, or deep plate, and then a powdered exothermic reaction layer is transferred onto the layer of mucous or liquid.

The thickness of the exothermic reaction layer or reaction auxiliary layer may be controlled simply and accurately by controlling transfer, screen printing, or plate depth in the case of gravure.

Where the exothermic reaction layer or reaction auxiliary layer is formed in the manner noted above, i.e., printing such as transfer, screen printing, gravure and so on, the exothermic reaction layer or reaction auxiliary layer is formed to be in the order of 0.02 to 1.5 mm, preferably 0.05 to 1 mm, and especially 0.1 to 0.5 mm. This allows the exothermic composition to be far thinner than in the prior art.

Among the above methods of forming the exothermic reaction layer or reaction auxiliary layer, transfer, screen printing or gravure is recommended from the point of view of realizing a precise thickness with ease and a shortened processing time. Particularly recommendable is transfer a which is suited for fine patterning and continuous formation.

In carrying out the transfer, the receiving surface of the film or sheet at one surface should preferably be roughened to enhance transferability. It is particularly desirable to use a liquid absorptive or water absorptive film or sheet such as of woven fabric or nonwoven fabric.

The method of forming a mucous reaction auxiliary layer and then forming a powdered exothermic reaction layer on the film or sheet may employ, for example, spraying instead of transfer. However, to avoid dust generation, a transfer method is preferred in which the exothermic reaction layer is borne by a carrier such as a transfer roller contactable with the reaction auxiliary layer to transfer the exothermic reaction layer.

A recommended method of causing the carrier to carry the exothermic reaction layer is use of magnetic attraction or electrostatic attraction which easily secures a uniform thickness and a uniform ingredient distribution of the exothermic reaction layer.

That is, where iron powder is used for the exothermic reaction layer and this exothermic reaction layer is placed in contact with a magnetized transfer roller, an adhering amount of the exothermic reaction layer may be uniformly applied by controlling the strength of a magnetic force. The adhering amount of the exothermic reaction layer may be uniformly applied with greater accuracy by leveling it with a blade as necessary.

Where an exothermic substance is placed in contact with a transfer roller with a charged surface, an adhering amount of the exothermic substance may be uniformly applied by controlling the strength of an electrostatic attraction. The adhering amount of the exothermic substance may be uniformly applied with greater accuracy by leveling it with a blade as necessary.

When the uniformly adhering exothermic reaction layer is pressed upon the reaction auxiliary layer by the transfer roller, the exothermic reaction layer contacting the reaction auxiliary layer adheres to the reaction auxiliary layer by the surface tenacity of the reaction auxiliary layer. The part of exothermic substance, which has not been transferred to the reaction auxiliary layer and remains on the transfer roller, will be collected, to prevent if from scattering to the circumference.

Since the exothermic reaction layer and reaction auxiliary layer are uniform over entire surfaces thereof, the thickness and dispersion of the exothermic reaction layer transferred from the transfer roller are uniform to a very high degree. Moreover, the layer may be formed thin, for example, in the order of 0.1 to 0.5 mm. In addition, the exothermic reaction layer adhering to the reaction auxiliary layer is tacked by the reaction auxiliary layer to be immovable within the pouch. This provides a product of highly reliable quality.

Moreover, the amount of transfer of the exothermic substance is controllable by a contact pressure of the transfer roller. It is therefore possible to detect a water content of the reaction auxiliary layer formed beforehand on the film or sheet, and adjust the pressing force of the transfer roller in real time in response to the water content, to stabilize the ingredient compounding ratio. This provides a product of highly reliable quality.

In the case of magnetic attraction, a magnetic region may be patterned by embedding a magnetic mat of desired shape, such as a mat of synthetic resin, rubber or the like mixed with magnets, in the surface of the transfer roller. In this way, a transfer region of metal powder may be patterned to a desired shape.

In the case of electrostatic attraction, an adhering region of carbon powder may be patterned to a finer degree than the exothermic substance by patterning a charge region comprising an insulator on the surface of the transfer roller, or by laser irradiation to a charged surface of the transfer roller to vary charge potentials regionally.

It is of course possible to use both magnetic attraction and electrostatic attraction where the exothermic reaction layer includes metal powder which is a magnetic substance.

Carbon powder or powder of a metallic chloride which is not a magnetic substance may be patterned by using electrostatic attraction to uniformly disperse it in a predetermined region, and prevented from scattering to the circumference.

That is, in a preferred method, a transfer roller is charged to attract carbon powder or powder of a metallic chloride. The transfer roller carrying the carbon powder by electrostatic attraction is rotated while pressing upon the layer of liquid or layer of mucous under an appropriate pressure. The carbon powder is transferred onto the surface of the reaction auxiliary layer by the surface tenacity of the reaction auxiliary layer.

Thus, for causing a mixture of a metallic powder and carbon powder, i.e., an exothermic reaction layer, to adhere to a predetermined region of the film or sheet, a magnetic mat and a surrounding insulating frame of suitable width may be embedded in the surface of a transfer roller which is an electric conductor. Then, the metal powder is transferred to the region of magnetic mat, and the carbon powder or the chloride powder to the region of the insulating frame, both in a uniformly dispersed state, and that without scattering dust to the circumference.

In the case of a metallic chloride, as it is easily and uniformly dispersible in water, an easy and inexpensive patterning may be effected in a uniform dispersion in a predetermined region, while reliably avoiding scattering to the ambient, by a method in which the chloride is dissolved in a liquid reaction auxiliary layer comprising water acting as a medium. It has also been found that carbon powder including fine particles is easy to handle when it is mixed into a liquid reaction auxiliary layer while reliably preventing dust generation.

Where the reaction auxiliary layer is formed in a plurality of layers, the sequence of in which layers of liquid and powder are alternately formed may be repeated. For example, the exothermic composition may be formed in a sequence in which first reaction auxiliary layer including water and a tenacity controller, second reaction auxiliary layer comprising a layer of carbon powder, a third reaction auxiliary layer having a water retainer added to a metallic chloride with water acting as a medium, and an exothermic reaction layer comprising a layer of metal powder are formed one over the other in this order.

A manufacturing time may be shortened significantly by forming an exothermic reaction layer and a single or a plurality of reaction auxiliary layers by transfer, screen printing, or gravure. The exothermic device may be manufactured by moving the film or sheet at high speed, e.g. 160 meters or more per minute.

The whole exothermic device can be formed to have a thickness in the order of 0.5 to 2 mm. Thus, the exothermic device is ultra-thin, has a uniform thickness, is soft and readily conformable to any curved or uneven areas of the human body or the like, readily follows expansions and contractions of surfaces of the human body or the like, and is free from movement of the exothermic composition in the pouch during use to give a comfortable feel to the wearer.

After the exothermic composition has been formed on a film or sheet at one surface or application surface having gas-permeability, another film or sheet over the exothermic composition to form an application surface or another gas-permeable surface, after then, by sealing these films or sheets at the entire circumference of the exothermic composition the exothermic device is completed. The exothermic device is inserted into a flat pouch made of a gas-tight synthetic resin film or sheet, to be treated as a product.

[Description of the Application Pad of the Present Invention]

The exothermic device according to the present invention is useful as an application pad, especially when an adhesive layer is laid on one side of the device.

In the pad according to the present invention, the film or sheet for forming an application surface of the pouch may be a gas-permeable film or sheet. However, a gas-tight film or sheet is preferred in order to enhance insulating effect based on tight sealing and heating effect of the exothermic device.

The gas-permeable or gas-tight film or sheet will not particularly be described to avoid tautology.

The adhesive layer used in the present invention is not limited as long as it adheres to clothing such as underwear or directly to an integument of the human body to support the exothermic device.

Thus, the adhesive layer may be an adhesive layer toward the skin, i.e. a skin adhesive layer. The skin adhesive layer may be a compress layer or adhesive layer, for example. The compress layer may be a known product which may or may not contain water.

In the sticking pad according to the present invention, the adhesive layer is preferably a untransferable adhesive to prevent it from remaining on a body surface or clothing when it is removed. Preferably, this pad is soft to be easily conformable to a body surface or clothing, and elastic to follow the following movement of a body surface or clothing easily. In addition, the pad should preferably have no unpleasant smell to give no unpleasant feeling to the user.

In the present invention, the skin adhesive layer may advantageously include skin absorbable medicine to improve a local therapeutic effect, to improve a general therapeutic effect, or to enhance a therapeutic effect of the medicine the blood or by promoting the circulation of the like with heating effect.

In this case, a layer containing skin absorbable medicine may have no adhesive property. Then, the skin adhesive layer should preferably include a layer containing skin absorbable medicine formed regionally thereon. It is particularly preferable to have a layer containing skin absorbable medicine regionally and independently of the skin adhesive layer.

Specifically, a layer containing skin absorbable medication may be formed independently and regionally in a central region of the skin adhesive layer or over the entire skin adhesive layer.

The medication used in the present invention is not limited as long as it is skin absorbable. Specific examples thereof include a skin stimulant, anodyne/antiphlogistic, central nerve active agents (soporific/sedative, anti-epileptic, psychoneurotic agent), diuretic, hypotensive, coronary vasodilator, throat pastille/expectorant, antihistaminic, antiarrhythmic, cardiac, adrenocortical hormone drug, and local anesthetic.

One type of these medicines, or two or more types thereof, as necessary, is/are used.

The amount of medication contained is not limited as long as a medical effect is expected. However, from the point of view of pharmacological effect, economy and adhesion, a content of the skin absorbable medicine is determined in the range of 0.01 to 25 parts by weight, and especially 0.5 to 15 parts by weight, in relation to 100 parts by weight of the adhesive.

According to the present invention, a water absorbent (water retainer) such as an water absorptive polymer may be added to the skin adhesive layer. In this case, a body fluid such as blood seeping from a wound and a secretion such as sweat are absorbed to prevent wetness of an affected part. Further, appropriate moisture and heat may be given to a body surface from the water retainer, heated by the exothermic device for a warm compress effect. The adhesive power of the skin adhesive layer may be prevented from lowering over a long period.

The adhesive layer used in the present invention may be applied directly to one surface of the exothermic device according to the present invention noted above. However, it is preferred that the adhesive layer is applied through a carrier film or carrier sheet such as paper, woven fabric, nonwoven fabric, foam sheet or the like in order to enhance adhesion of the adhesive to the exothermic device. This carrier film or carrier sheet may be fixed to the exothermic device by using an adhesive or hot melt adhesive.

Where the adhesive layer is applied directly to one surface of the exothermic device according to the present invention, the adhesive layer receiving surface of the exothermic device may be roughened to enhance adhesion of the adhesive layer to the exothermic device. However, the adhesive layer may be made removable for repeated use or the adhesive layer may be made changeable appropriately.

To render the adhesive layer separable, a tenacity controller which lowers adhesive power may be dispersed over one or both of an adhesive surface of the adhesive layer opposed to the exothermic device and an adhesive layer receiving surface of the pouch. Alternatively, one or both of the adhesive surface of the adhesive layer opposed to the exothermic device and an adhesive layer receiving surface of the pouch may be formed uneven.

The tenacity controller may be a substance having a non-adhesive property contrary to the adhesive, and preferably having a blooming property. Examples of such controller include silicone, polyethylene wax, surface active agent and paraffin.

The application pad in the present invention may employ a single-side adhesive tape having a backing which is removably applied to the adhesive layer formed on the exothermic device, and an adhesive layer attached to an application surface of the backing and removably applied to the application surface, to facilitate separation of the exothermic device from the adhesive layer, or may employ a double-coated tape having opposite adhesive surfaces, which is removably applied to the film or sheet of the exothermic device and to a body surface or clothing.

Where the adhesive layer includes a backing and adhesives attached to opposite surfaces thereof, the backing may be in film, sheet or cloth form. Its material is not limited but preferably has a certain degree of durability to withstand repeated use. Specifically, what are usable are natural or synthetic rubber, synthetic resin, natural fiber, synthetic fiber, a nonwoven fabric or woven fabric of a mixture thereof, and paper.

Specific examples of the above synthetic resin include polymeric materials such as polyethylene, polypropylene, polyamide, polyester, polyvinyl chloride, polyvinylidene chloride, polyurethane, polystyrene, saponified ethylene-vinyle acetate copolymer and ethylene-vinyle acetate copolymer.

Preferably, the backing of the adhesive layer is soft to be easily conformable to unevenness of a body surface or clothing. Further, it should preferably have elasticity to be capable of following any movement of a body surface or clothing.

In addition, the backing of the adhesive layer is preferably gas-tight in order to enhance the heating effect. Where the backing is applicable directly to an integument, a skin instimulative material should be preferably selected for use in order to avoid an allergic inflammation of the integument.

From these points of view, polyethylene, polypropylene, polyurethane and polyvinyl chloride are preferred materials among the above synthetic resins.

An adhesive layer in film or sheet form made of an adhesive alone is preferred in view of enhancing conformability and following capability with respect to a surface to which it is applied, and in view of enhancing the heating effect based on its gas tightness. Further, a skin instimulative material is preferred in order to avoid causing an allergic inflammation of the integument.

The adhesive used in the adhesive layer shows a lasting, strong tenacity (tackiness) at room temperature and in solvent-free condition. It firmly adheres to an integument or clothing simply by pressing lightly with a finger. It has an appropriate adhesive power or holding strength and an appropriate tenacity, while having sufficient cohesion and elasticity. It may be handled with fingertips, and may be removed from a smooth object to which it has been applied, without adhesive transfer.

The adhesive basically includes an elastic polymer providing cohesion and a tackifier, these two components acting as skeleton, with a tenacity controller, adhesion improver, stabilizer, colorant, ultraviolet inhibitor, antimold, antifoaming agent, thickener and antioxidant added thereto in order to provide various resistances. The elastic polymer is classified into a diene elastic material, an ethylenic elastic material or a condensed elastic material.

An adhesive using a diene elastic material is called a rubber adhesive which include rubber and tackifier in the ratio of 1:0.5 to 2.

The rubber mainly used is a block copolymer, reclaimed rubber or thermoplastic rubber such as natural rubber (NR), polyisoprene, styrene-butadiene rubber (SBR), butyl rubber (BR), styrene-isoprene-styrene (SIS) or styrene-butadiene-styrene (SBS).

The most typical example of ethylenic elastic material is an acrylic polymer also called an acrylic adhesive. The acrylic polymer acting as a base of the acrylic adhesive, generally, expresses adhesion by itself and does not require a tackifier. The monomers constituting the polymer, broadly, comprise three components, one acting as an adhesive component, another acting as cohesive component and the other acting as a modifying component.

A preferable adhesive component is alkyl ester alkylate with an alkyl group having carbon number 4 to 10. Tg is low in the order of $-20°$ to $-70°$ C. Typical examples are alkyl esters of $C_2$ or more, such as ethyl acrylate, butyl acrylate, octyl acrylate, 2-ethylhexyl acrylate, and n-butyl acrylate.

This adhesive component is used as a main component, which is highly adhesive but lacks in cohesion, thus requiring a cohesive component. The cohesive component may comprise a monomer which is copolymerizable and has a high Tg, e.g. (1) an ester acrylate of low alkyl group of $C_1$ to $C_3$ such as methyl acrylate, ethyl acrylate or methyl methacrylate, (2) an alkyl ester such as alkyl methacrylate of $C_2$ to $C_8$, (3) a vinyl ester of $C_1$ to $C_3$ such as vinyl acetate or vinyl propionate, (4) acrylonitrile, (5) styrene, and (6) a vinyl monomer such as vinylidiene chloride. The cohesive component not only increase cohesion but sometimes contributes toward improved performance such as improved adhesion, improved water resistance or improved transparency, and is used to impart a special feature of the adhesive.

The modifying component generally comprises a functional group copolymerizable with adhesive components and cohesive components. Examples thereof include (1)

unsaturated carboxylic acids such as acrylic acid, methacrylic acid and maleic anhydride, (2) unsaturated acid amides and modifications such as acrylamide and acrylamide derivatives, (3) hydroxyl group containing monomers, (4) acrylonitrile, (5) hydoxyethyl acrylate and (6) glycidyl acrylate. The modifying component is of course useful for crosslinking, but is also useful in improving adhesion and expediting reactions during polymerization.

An acrylic adhesive basically includes the above three components, but can be formed of one component or two components. Further, an acrylic adhesive comprising a single component has a high degree of transparency and excellent durability, and is used mainly as an emulsion type and solvent type adhesives.

The ethylenic elastic material may comprise a vinyl ether elastic material in place of an acrylic polymer as noted above. The adhesive employing a vinyl ether elastic material is called a vinyl adhesive, and is formed of alkyl vinyl ether polymer of $C_2$ to $C_4$. The vinyl adhesive has a mixture of high molecular weight and low molecular weight compounds to maintain a balance of adhesion, tenacity and tackiness. However, other resins may be used as well to increase tackiness and adhesion.

The adhesive employing a condensed elastic material is called a silicone adhesive. The silicone adhesive has polydimethyl siloxane rubber as a main component thereof, and a silicone resin of low molecular weight including dimethyl siloxane is added to the polydimethyl siloxane rubber. The rubber-like siloxane provides a film form and film cohesion, while the silicone resin provides tackiness and adhesion. The silicone adhesive is usable over a wide temperature range, and has excellent heat resistance and durability.

The tackifier may be classified into a tackifying resin, plasticizer, oil and fat, macromolecular low grade polymer, crosslinking agent, adhesion improver, filler or other compound.

The tackifying resin comprises one having a molecular weight in the order of 1000, such as rosin which is a natural resin, rosin modification, derivative of rosin or modified rosin, coumarone-indene resin, terpene resin (polyterpene), terpene modification, aliphatic hydrocarbon resin, cyclopentadiene resin, aromatic petroleum resin, non-reactive phenol resin, styrene resin, xylene resin, or vinyltoluene-α-methyl styrene copolymer. Generally speaking, many are solid resins, but there are liquid resins such as hydrogenated rosin and its esters. The tackifier must be highly compatible to the elastic material used, and must provide tackiness, the compatibility being a source of tackiness. Further, the tackifier should preferably not be easily oxidizable. From this point of view, what are recommendable are hydrogenated rosin among the rosin type, polyterpene, and petroleum resin of the $C_5$ and $C_9$ types.

To provide cohesion or tackiness, the type and melting point of the tackifier are actually selected according to the type of elastic material. Two or more tackifying resins are used sometimes.

The plasticizer, generally, has properties to increase workability, softness, elasticity and flexibility and to improve softness and rubber-like elasticity at low temperature. However, it is difficult to express, by itself, tackiness which is the essential characteristic of an adhesive, the plasticizer is often used with a tackifying resin or the like.

Examples of the plasticizer include a phthalic acid plasticizer, phosphoric ester plasticizer, adipic acid ester plasticizer, sebacic acid ester plasticizer, ricinoleic acid ester, polyester type plasticizer, paraffin chloride and silicone. Macromolecular polyester increases softness at low temperature, while silicone is useful in improving tackiness at low temperature as well as plasticity at low temperature.

Oils and fats have the same function as plasticizers, and are used to add plasticity and to act as a tenacity controller or adhesion improver. Oils and fats include animal oils, vegetable oils, mineral oils and silicone oils, which are selectively used according to purpose. Oils and fats are desirable as compounding ingredients since they are inexpensive and increase plasticity, but there is a limitation to compounding amount since they rapidly lower the cohesion of the adhesive.

The macromolecular low grade polymer provides functions of its own as well as being used for the same purpose as the plasticizer or oils and fats. That is, this polymer is used for the purposes of tackifying, adhesion, resistance to cold, fluidity adjustment and so on. In polyvinyl ether and polyisoprene adhesives, it provides tackiness according to the degree of molecular weight of each polymer to maintain a balance of tenacity, holding strength and tackiness.

The macromolecular low grade polymer may be found in elastic materials and tackifying resins among adhesive raw materials in addition to the above. Examples thereof are SBS, BR, polyacrylic ester, hydrogenated rosin methyl ester among the rosin tackifying resins, low molecular styrene resin, and polyterpene.

The crosslinking agent is selected according to the elastic material used and what should be crosslinked. For rubber adhesives, generally, vulcanization (crosslinking) is effected by a sulfur-vulcanization accelerator. However, since a vulcanizing operation has various problems, in recent days, there are not a few cases in which aluminum alcoholate, polyisocyanate or zinc resinate is used for crosslinking alkyl phenol resin.

Crosslinking agents for rubber adhesives include sulfur compounds such as tetramethyl thiuram disulfide and dibutyl zinc thiocarbamide, simple substances such as selenium and sulfur, and fatty compounds such as oil soluble thermosetting phenol-formaldehyde resin, and methlol uric acid formaldehyde resin.

As distinct from rubber adhesives, acrylic adhesives have characteristics to facilitate introduction of functional groups into polymers. However, it is necessary to select a crosslinking method suited to the purpose since the performance of the adhesive is variable with crosslinking methods. A crosslinking method normally used for acrylic adhesives employs compounds of carboxylic acid/polyisocyanate, N-methylol acrylamide and glycylacrylate/amine, varied etherized aldehyde modified carboxylic acid amides, diketone/thermosetting phenol resin, epoxide and epoxy resin.

A filler compounded with natural rubber or synthetic rubber used in the adhesive reinforces rubber, improves tensile strength, tear strength, wear resistance and hardness, increases the volume and lowers cost. The grain size, surface area, state of aggregation, dispersion and so on of the filler greatly influence a reinforcing effect. This effect is considered due to an interaction between rubber molecule and filler which adjusts slippage between rubber and filler. The presence of the filler reduces the proportion of flowable ingredients by a corresponding amount, rendering them less flowable and less tacky. Thus, in use, the filler must be added, taking fluidity and compression resistance. In this case, silica gel is sometime used to control the fluidity and compression resistance of the filler.

Fillers used in rubber adhesives are classified broadly into inorganic fillers and organic fillers. Examples of inorganic fillers include metal powders such as of aluminum, copper, iron and lead, silica, silicate, silica rock, diatomaceous earth, alum such as alumina, lime such as calcium carbonate and gypsum, alumina-silica such as mica and clay, magnesia-silica such as talc and asbestos, carbons or carbites such as graphite, carbon black and white carbon, cement, antimony oxide, zinc oxide, and magnesium carbonate. Examples of organic fillers are vegetable natural substances such as linter, linen and sisal wood flour, animal natural substances such as silk, and man-made or synthetic substances such as viscose, acetate, polyamide, vinylon and vinyl chloride.

The filler has no function to add significant characteristics relating to adhesion unlike other materials in the compound of the adhesive, but specifically possesses functions to improve cohesion, increase compression resistance, improve tape rewinding, and control fluidity. However, the filler may be made to add adhesion and the like, thereby improving the function of the adhesive to a great extent, as the adhesion of polyolefin is improved by mixing silicone.

The rubber adhesive is highly self-adhesive and has a characteristic of its adhesion freely controlled as desired by compounding, but is inferior in durability to other adhesives. The rubber adhesive is used mainly as solvent type adhesive, and is given calendar coating or hot melt coating, but is rarely used as an emulsion. The rubber adhesive is a multi-ingredient type, and may therefore undergo influences of a solvent used, owing to a difference in solubility.

The stabilizer is used particularly for a vinyl adhesive or for a vinyl resin in the compound, and generally used for a chlorine-containing resin. Examples thereof include phenols and bisphenols, amines, sulfur compounds, phosphites, epoxy compounds and organic metallic salts.

The colorant is used in making the adhesive white, for example. Preferably, a desired color should be obtained with a small amount thereof since use of a large amount of pigment would affect tackiness. In the case of white, titanium oxide having high hiding power is extensively used, and so are zinc oxide and calcium carbonate.

The ultraviolet inhibitor, as is the antioxidant, is used to aging by light, such as yellowing or blackening by light, of transparent adhesive tape or the like. It is classified into a benzophenone type, salicylate type, benzotriale type, or substituted acrylonitrile type.

The antimold, antifoaming agent and thickener are used particularly for an emulsion type adhesive. Examples of the antimold are inorganic compounds such as arsenious acid, cuprous oxide and mercury oxide, and organic compounds such as organic mercury compounds, organic sulfur compounds, phenol compounds and organic copper compounds. Inorganic mercury compounds and organic mercury compounds have very strong antimold action, but are currently out of use because they are highly toxic and unsafe to use.

Silicone emulsion and alcohols are known as antifoaming agents. These substances have a releasing property (lubrication) as well as an antifoaming effect, and lowers tackiness when used in excess. It is therefore necessary to select an antifoaming agent which is effective even in a small amount.

The thickener is intended to increase the viscosity of an emulsion, and generally a water-soluble polymer or colloid are used. These are selectively used according to types of emulsion. For example, casein or the like is used for rubber latex such as SBR or NR. PVA, polyacrylic soda, CMC or methyl cellulose is used for an acrylic or vinyl emulsion. The thickener not only increases viscosity but gives stability to the emulsion. It is therefore necessary to select a suitable thickener. It is also necessary to give full consideration to the fact that the thickener is a macromolecular substance included in the adhesive layer, and naturally therefore influences adhesion.

The rubber adhesive, acrylic adhesive and silicone adhesive can be invariably stripped of dust and other foreign matters adhering to their surfaces by rinsing, and recover adhesion after drying. Thus, any one of them may be used. However, the acrylic adhesive is preferred because of its outstanding characteristics to have adhesion lowered by rinsing, the adhesion being recovered after drying. Among acrylic adhesives, one having polyacrylic gel in sheet form is desirable.

Where the adhesive layer is a double-coated tape, the adhesive opposed to the exothermic device may include a substance, e.g. silicone, polyethylene wax, surface active agent or paraffin, which is non-adhesive as distinct from the property of the adhesive, and preferably has a blooming property.

By adding such a substance and by surface treatment of adhesive surfaces, adhesive layers sticking to each other may be adapted separable. In this case, two exothermic devices may be attached to one adhesive layer, and the adhesive layer may be folded over in a sticking state for storage, with the exothermic devices arranged outside, or a plurality of adhesive layers may be stacked one upon another for storage. Moreover, when the adhesive layer is applied as folded, by mistake, it may simply be peeled off and spread.

The adhesive surface of the adhesive layer opposed to the exothermic device may be formed uneven to facilitate separation from the exothermic device.

In addition, where the adhesive layer is a skin adhesive layer, the skin adhesive layer may contain a magnetic element and or a far infrared radiator. A magnetic element may be inserted between the adhesive layer and exothermic device to produce an effect of magnetic therapy. A far infrared radiator which radiates far infrared rays having a wavelength of 4 to 16 $\mu$m depending on the heat of the exothermic device or body temperature, is employed to produce a heating effect based on the far infrared rays.

In the present invention, where two or more of the skin absorbable medicine, far infrared radiator and magnetic element are included in the adhesive layer or between the adhesive layer and exothermic device, the therapeutic effects are synergized to produce a higher therapeutic effect than where any one of them is used alone.

The far infrared radiator, preferably, radiates far infrared rays having a wavelength in the order of 4 to 16 $\mu$m depending on a human body temperature or a slightly warmer heat of the exothermic device than body temperature. For example, the far infrared rays having the above wavelength may be generated by combining inorganic oxides such as $Fe_2O$, $FeO$, $Fe_2O_3$, $SiO_2$, $Al_2O_3$, $ZrO$, $ZrO_2$, $BeO$, $V_2O_3$, $V_2O_5$, $Y_2O_3$, $CoO$, $CuO$, $Cu_2O$, $NiO$, $Ni_2O_3$, $MnO$, $MnO_2$, $MgO$, $TiO$, $TiO_2$, $ZnO$ $ThO_2$, $Na_2O$, $K_2O$, $CaO$ and $BaO$.

Specific examples are a complex having $2MgO.2Al_2O_3.5SiO_2.Fe_2O_3$ as a main ingredient thereof, a complex having $Li_2O.CuO.Al_2O_3.4SiO_2$ as a main ingredient thereof, and a complex having $Al_2O_3.TiO_2$ as a main ingredient thereof. The term having as a main component used herein is intended to mean the case of having only the state chemical composition as well as the case of having other ingredients besides such ingredient.

In the exothermic device and/or application pad according to the present invention, the pattern of the exothermic reaction layer may be the same as that of the reaction auxiliary layer, but the exothermic reaction layer may be formed in a gapped pattern on the reaction auxiliary layer, e.g. in a stripe pattern such as longitudinal stripes or transverse stripes, or in lattice pattern, broken lines or dots.

The exothermic reaction layer becomes solid and hard by exothermic reaction, and may therefore cause a skin stress when it was applied directly to an integument. Where the exothermic reaction layer is formed partly, the whole exothermic device is softened at locations where the exothermic reaction layer is not formed, to assure a further improvement in the feel of use.

By in a gapped pattern forming the exothermic reaction layer on the reaction auxiliary layer as noted above, overheating due to a stored heat may be prevented. Besides, temperature control is facilitated to prevent low-temperature burns with increased assurance.

The exothermic device according to the present invention is sealed in an outer pouch formed of gas-tight film or sheet to be treated as a finished product.

When the outer pouch of the product is opened, air contacts with the exothermic composition, and the exothermic composition begins to generate heat. After reaching a predetermined temperature within a short time, the exothermic composition continues to give heat at the predetermined temperature over a predetermined heating period.

In the exothermic device according to the present invention, as noted hereinbefore, the exothermic composition is formed in layers comprising at least one exothermic reaction layer having an exothermic substance as an essential ingredient thereof, and at least one reaction auxiliary layer including other ingredients. Thus, all the ingredients of the exothermic composition are never mixed before the exothermic reaction layer is inserted into a pouch. The exothermic device may therefore be handled in the atmosphere without a possibility of generating heat or becoming coagulated.

This eliminates various harmful effects due to the exothermic reaction or coagulation of the exothermic composition occurring at a time of manufacture. Besides, there is no possibility of a heat loss or lowering of quality due to heat generation during a manufacturing process or of a disruption of manufacture due to coagulation. Moreover, as each composition may be stored in a manufacturing apparatus over a long period, without coagulation the necessity of an irksome and ugly operation such as cleaning and washing done before an interruption of manufacture is eliminated.

Even when manufacture is stopped at any point of time, materials in process need not be removed from the manufacturing apparatus. It is unnecessary to extend an operation into a recess time or after a closing time in order to complete processing of the materials inside the manufacturing apparatus.

Since the materials in the manufacturing apparatus need not be discarded, a yield of materials is increased, and a high cost of waste disposal is avoided. This achieves a substantial reduction in cost.

Forming of the exothermic reaction layer and/or reaction auxiliary layer may be done successively from one surface. Specifically, forming of layers may be begun, for example, with the patterning an exothermic reaction layer or reaction auxiliary layer in a predetermined region of the gas-permeable or gas-tight film or sheet at one surface by a transfer, screen printing or spraying method. Next, an exothermic reaction layer or reaction auxiliary layer are transferred.

In this case, the thickness of the exothermic reaction layer or reaction auxiliary layer may be simply and accurately curbed by controlling a plate depth in the case of a transfer or screen printing.

Where the exothermic reaction layer or reaction auxiliary layer is formed in the manner noted above, the reaction auxiliary layer may be formed to be 0.2 to 2.5 mm to the exothermic reaction layer in the order of 0.01 to 1 mm, preferably, the reaction auxiliary layer in the order of 0.3 to 2 mm to the exothermic reaction layer in the order of 0.02 to 0.8 mm, and more preferably, the reaction auxiliary layer in the order of 0.5 to 1.75 mm to the exothermic reaction layer in the order of 0.03 to 0.6 mm. Thus, the exothermic composition may be formed much thinner than in the prior art.

The whole exothermic device formed to have a thickness in the order of 0.5 to 2 mm is ultra-thin, has a uniform thickness, is soft, causes little skin stress, is readily conformable to any curved or uneven areas of the human body or the like, readily follows expansions and contractions of a surface of the human body or the like, and is free from movement of the exothermic composition during use to give an excellent feel to the wearer.

The whole exothermic device formed to have a uniform thickness and to be thin as noted above facilitates control of heating time, hardly causes a low-temperature burn since very little overheating due to a heat stored in the exothermic composition occurs, and further diminishes temperature variations of the exothermic device, thereby stability of quality is achieved and the reliability is improved greatly.

In particular, the whole exothermic device is transferred and sealed in an ultra-thin form in the order of 0.5 to 2 mm, by which perfect deaeration is achieved. Further, where the reaction auxiliary layer is transferred to a nonwoven fabric inside the film or sheet on the front or back or both surfaces of a covering material, the reaction auxiliary layer is caught by to the nonwoven fabric by virtue of its tackiness. The exothermic reaction layer is also fixed to the reaction auxiliary layer by the tackiness of the reaction auxiliary layer. Since the exothermic composition is sandwiched, the exothermic composition is prevented from movement within the covering material during use or transport. This prevents other movements of the exothermic composition also, e.g. a movement occurring just before termination of heat generation, and a movement occurring when heating temperature becomes high under the influence of ambient temperature.

Furthermore, a product of highly reliable quality is provided since the exothermic reaction layer and auxiliary layer are formed to have uniform thicknesses with ease and since the ingredients are uniformly dispersed. This also enables high-speed processing to manufacture a large quantity of product in a short time.

The application pad according to the present invention employs the exothermic device according to the present invention as an exothermic device. Therefore, besides the foregoing functions, the exothermic device is applicable to an integument or clothing for use.

In this case, a magnetic element and/or far infrared radiator may be included in the exothermic reaction layer, in the (skin) adhesive layer or between the exothermic device and (skin) adhesive layer, to improve or express a heating effect or an effect of magnetic therapy. The skin adhesive layer may contain skin absorbable medication, or a layer containing skin absorbable medication may be formed independently of the skin adhesive layer, to express a general or local pharmacological effect.

Particularly when the pad is applied directly to the skin, a design for skin temperature plus some degrees is facilitated by controlling the thickness(es) of the exothermic reaction layer and/or reaction auxiliary layer. As a result, a low-temperature burn is avoided with increased assurance.

Other features and advantages of the present invention will be apparent from the following description.

DETAILED DESCRIPTION OF THE PREFERRED EMBODIMENTS

Embodiment 1

Figure 1:
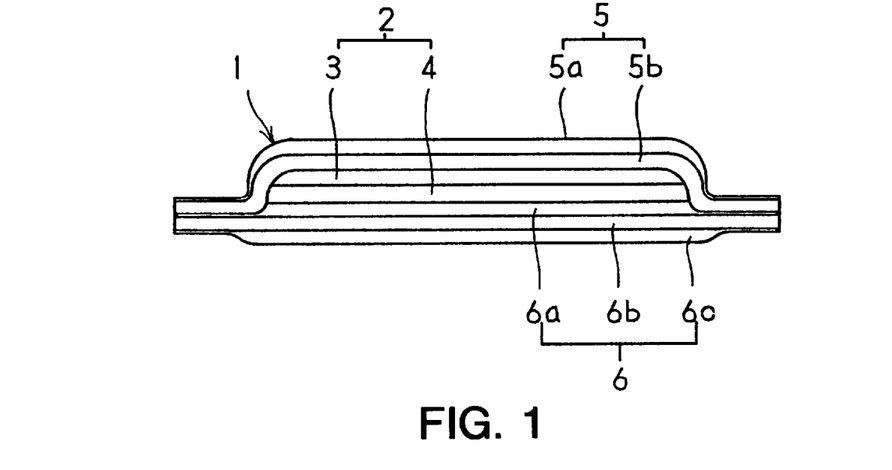
FIG. 1 is a schematic view of an exothermic device in one embodiment of the present invention.

Referring to FIG. 1, the exothermic device in this embodiment is in rectangular form 130 mm×95 mm. This exothermic device has an exothermic composition 2 enclosed in a flat film pouch 1 at least one surface of which is gas-permeable. The exothermic composition 2 is formed in two layers, one of an exothermic reaction layer 3 including iron powder, and which is the other one of which is a single reaction auxiliary layer 4 including other ingredients. The exothermic composition 2 is enclosed in the pouch 1 formed of a film having gas-permeability (gas-permeable film) 5 and a backing film 6, and is arranged to contact ambient air through the gas-permeable film 5.

The pouch 1 will serve the purpose if it is a pouch with a necessary mechanical strength such as tensile strength and having at least one surface thereof formed of gas-permeable flat film or sheet. However, it is soft so as to be easily conformable to unevenness of a body surface or clothing.

The pouch 1 has at least one surface thereof formed of gas-permeable flat film or sheet in order to allow the exothermic composition 2 enclosed therein to contact oxygen in the atmosphere. The pouch may be formed by doubling or tripling and heat-sealing a single gas-permeable film or sheet. Alternatively, the pouch may be formed by placing, a single gas-permeable film or sheet and a single gas-tight film or sheet one over the other with the exothermic composition 2 therebetween and joining the peripheries thereof by heat sealing or with a hot melt type adhesive. In this embodiment, the pouch 1 is formed by placing, over the exothermic composition 2 placed on the single gas-permeable film 5 and a gas-tight backing film 6 and heat-sealing the peripheries of the film 5 and backing film 6.

However, the gas-permeable film 5 and gas-tight backing film 6 are joined together after the exothermic composition 2 is formed on the backing film 6 as described later.

In this embodiment, the following materials were used for the gas-permeable film 5 forming the pouch 1.

A porous reinforcing polyamide backing film (nonwoven fabric, basis weight: 40 g/m$^2$) 5a was laminated on one surface of a gas-permeable polyethylene backing film (thickness: 40 μm) 5b [moisture permeability by the cup method (JIS Z 0208: at 40° C. and 90% relative humidity): 350 g/m$^2$.24 hr].

The following materials were used for the gas-tight backing film 6 forming the pouch 1.

Rayon/polyester nonwoven fabrics 6a and 6c with a rayon fiber content of 60% by weight and a basis weight of 40 g/m$^2$ were laminated on opposite surfaces of a polyethylene film 6b having a thickness of 40 μm.

In manufacturing the exothermic device according to the present invention, the reaction auxiliary layer 4 having a thickness of 480 μm was first formed on the rayon/polyester nonwoven fabric 6a of backing film 6 by screen-printing with a reaction auxiliary ink once which had been formed of a reaction auxiliary described later. Thereafter, the exothermic reaction layer 3 having a thickness of 30 μm was formed by transferring onto the reaction auxiliary layer 4 made of iron powder as an exothermic substance and a highly water-absorptive resin.

Next, the gas-permeable film 5 was laminated on the exothermic reaction layer 3 of the exothermic composition 2 formed on the backing film 6, so that the gas-permeable backing film 5b of the gas-permeable film 5 is in contact therewith at their periphery. The four peripheral edges of the laminate were heat-sealed to obtain the exothermic device (thickness: 1100 μm) according to the present invention.

The exothermic composition including the exothermic reaction layer and reaction auxiliary layer formed as above has the following ingredients:

(1) The exothermic reaction layer (30 μm) included iron powder (DKP manufactured by Dowa Teppun) and a highly water-absorptive resin (CS-6H manufactured by Nihon Shokubai). The iron powder was 65% by weight of the whole exothermic composition. The highly water-absorptive resin was 2% by weight of the whole exothermic composition.

(2) The reaction auxiliary layer (480 μm) had the following composition. This reaction auxiliary layer was 33% by weight of the whole exothermic composition.

The weight percentage of each ingredient represents a proportion in relation to the whole exothermic composition.

carbon powder
    fine powder of activated carbon (Activated Carbon GL-50 manufactured by Noritt) 7% by weight water retainer
    nonionic water-soluble cellulose ether (Metolose SM-4000 manufactured by Shinetsu Kagaku)

|  |  |
| --- | --- |
|  | 1% by weight |
| sodium chloride | 2% by weight |
| water | 23% by weight |

In manufacturing the reaction auxiliary ink for use in screen printing by mixing the ingredients of the reaction auxiliary layer, Metolose powder acting as water retainer, fine powder of activated carbon and sodium chloride powder were mixed and then water was added to obtain a uniform reaction auxiliary ink.

That is, the proportions of ingredients of the whole exothermic composition were, roughly, 65% by weight of iron powder, 7% by weight of carbon powder, 2% by weight of water retainer (highly water-absorptive resin), 2% by weight of sodium chloride and 23% by weight of water.

In the present invention, the whole exothermic device can be formed to have a thickness in the order of 0.5 to 2 mm. Thus, the exothermic device is ultra-thin, has a uniform thickness, is soft, gives little skin stress, is readily conformable to any curved or uneven areas of the human body or the like, readily follows expansions and contractions of surfaces of the human body or the like, and is free from movement of the exothermic composition during use to give a comfortable feel to the wearer.

Embodiment 2

Figure 2:
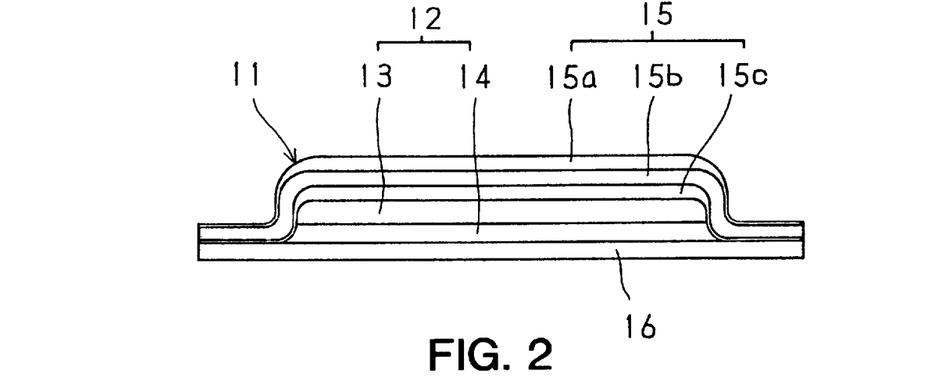
FIG. 2 is a schematic view of an exothermic device in a further embodiment of the present invention.

An exothermic device in a different embodiment of the present invention shown in the schematic view of FIG. 2 includes a pouch 11 formed of a gas-permeable film 15 having a three-layer laminated film structure with a synthetic resin film 15b sandwiched between two, inner and outer, layers of nonwoven fabric 15a and 15c, and a backing film 16 which is a synthetic resin film. The other aspects are the same as in Embodiment 1, and will not particularly be described to avoid tautology.

Embodiment 3

Figure 3:
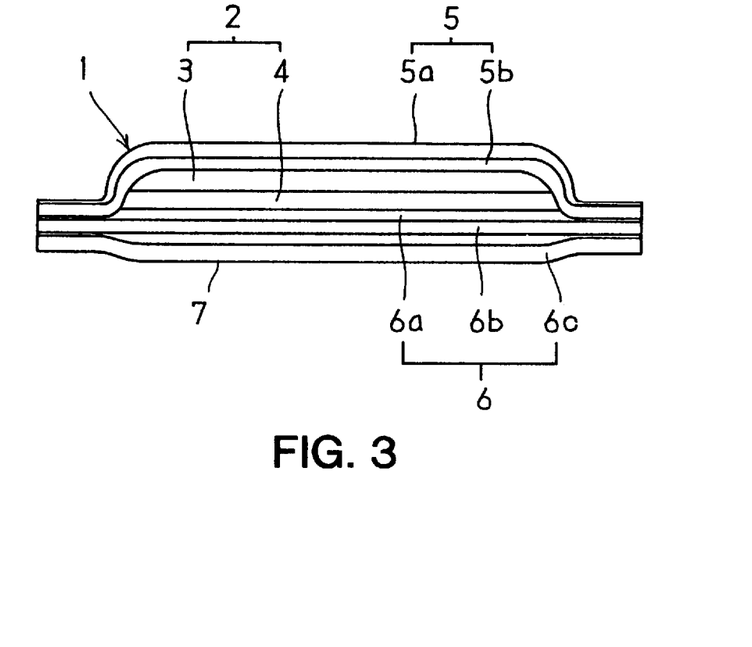
FIG. 3 is a schematic view of an exothermic device in a still further embodiment of the present invention.

An exothermic device according to the present invention shown in the schematic view of FIG. 3 is obtained by the following method.

This exothermic device is manufactured as in Embodiment 1 except that a skin adhesive layer 7 applicable to an integument is formed on an exposed surface of the backing film 6 in Embodiment 1.

In this case, the skin adhesive layer 7 is an adhesive layer obtained by the following method and having a thickness of 100 μm.

A uniform fused mixture of 35 parts by weight of styrene-isoprene-styrene block copolymer, 27.5 parts by weight of hydrogenated petroleum resin, 6.5 parts by weight of terpentine resin, 18.5 parts by weight of paraffinic oil, 6.5 parts by weight of aromatic oil, 3.5 parts by weight of titanium oxide, 2 parts by weight of zinc white and 0.5 parts by weight of tris-nonylphenyl-phosphite is formed into a film having a thickness of 100 μm by fused extrusion from a T-shaped nozzle (T-die).

Embodiment 4

A pad according to the present invention was obtained by the following method.

A lidocaine hydrochloride containing adhesive layer was formed by coating lidocaine hydrochloride jelly on the skin adhesive layer 7 in Embodiment 3. In this case, the whole lidocaine hydrochloride containing adhesive layer contained 1.5% by weight of lidocaine hydrochloride.

Embodiment 5

Figure 4:
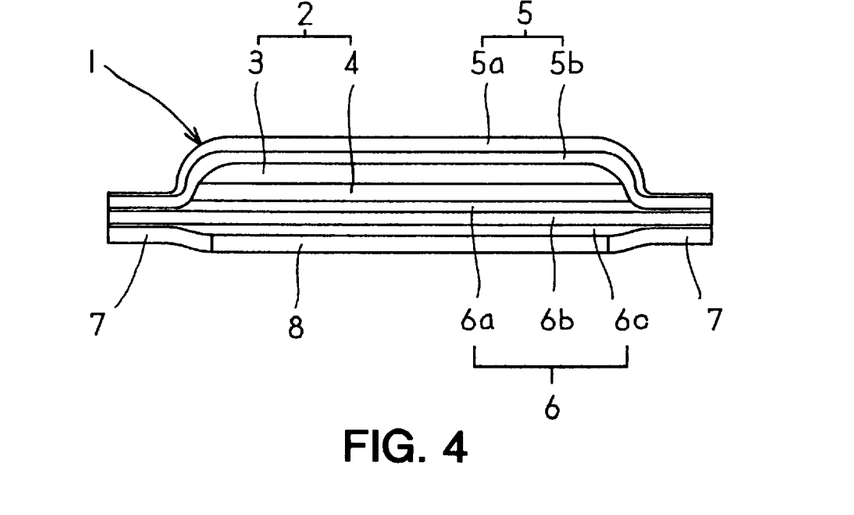
FIG. 4 is a schematic view of a sticking pad in one embodiment of the present invention.

A pad in a further different embodiment of the present invention as shown in the schematic view of FIG. 4 includes, around an exothermic device, a skin adhesive layer 7 formed of the same adhesive as used in Example 3, and a lidocaine hydrochloride jelly (lidocaine hydrochloride content: 2% by weight) layer 8 formed inwardly thereof.

Comparative Example 1

A skin adhesive layer (thickness: 100 μm) as in Embodiment 3 was formed on one surface of a usual exothermic device on the market (rectangle 130 mm×95 mm).

This exothermic device had a total thickness of approximately 3 mm.

Comparative Example 2

A lidocaine hydrochloride containing adhesive layer was formed by coating lidocaine hydrochloride jelly, as in Embodiment 4, on the skin adhesive layer in Comparative Example 1. In this case, the whole lidocaine hydrochloride containing adhesive layer contained 1.5% by weight of lidocaine hydrochloride.

The pads of Embodiments 4 and 5 and Comparative Examples 1 and 2 were applied to patients (10 males and 5 females aged 55 to 65) complaining of leg pains, to conduct tests in respect of adhesion, application feel, conformability to uneven surfaces of the human skin, subjective symptom of leg pain and low-temperature burn.

In this case, one pad was applied to a site of leg pain, which was changed every day for one week.

All of these embodiments and comparative examples gave good results in respect of adhesion.

All patients claimed that the pads in Embodiments 4 and 5 were ultra-thin, had a uniform thickness, were soft, gave little skin stress or tight feel, were readily conformable to uneven areas of the human body, and gave them a comfortable feel.

Regarding the pad in Comparative Example 1, one of the 15 patients claimed that it peeled at the corners during use, and four of the 15 patients claimed that it gave skin stress and a tight feel, had poor conformability to uneven areas of the human body, and gave them an uncomfortable feel. Regarding the pad in Comparative Example 1, three of the 15 patients claimed that it peeled at corners during use, and two of the 15 patients claimed that it gave skin stress and tight feel, had poor conformability to uneven areas of the human body, and gave them an uncomfortable feel.

A comparison made in pharmacological effect between Embodiment 4 and Comparative Example 2 showed that Embodiment 4 had an outstanding pharmacological effect compared with Comparative Example 2.

The reason is not clear, but it is understood that the pad in Embodiment 4, compared with that in Comparative Example 2, had excellent skin absorption of lidocaine hydrochloride since the pad was ultra-thin and soft, was readily conformable to uneven areas of the human body, and had excellent adhesion to the skin.

Figure 5:
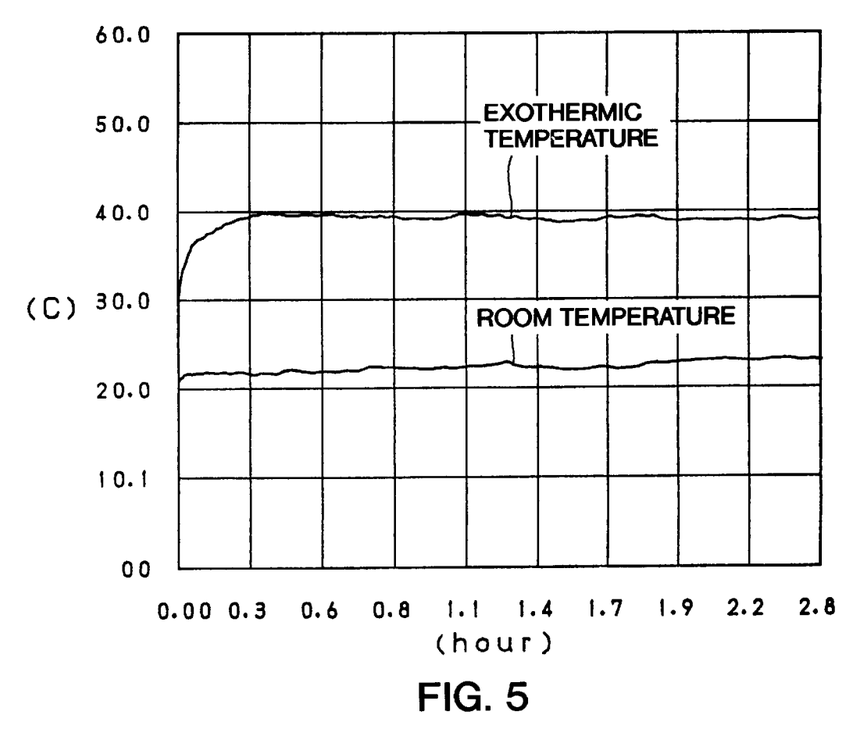
FIG. 5 is a view showing exothermic temperature characteristics of the pad in the embodiment of the present invention.

The pad in Embodiment 3 was applied to the back, and temperature variations on the back were recorded with SBR187-35CA of Rika Kogyo Kabushiki Kaisha, using five thermocouples. It has been found that an exothermic temperature of 38° to 39.7° C. continues at a room temperature of 21° to 23° C. as shown in FIG. 5.

One pad of Embodiment 3 or Comparative Example 1 was applied to the back (patients: 15 healthy adult males aged 25 to 35), which was changed every day for one week.

Peeled positions of the pads in Embodiment 3 and Comparative Example 1 were observed with the naked eye when changing the pads. No low-temperature burns were detected in the case of Embodiment 3, but low-temperature burns were detected with two of the 15 patients in the case of Comparative Example 1.

The reason is not clear, but it is understood that of the pad in Embodiment 3 caused no low-temperature burn since the whole exothermic device was thin and minimal overheating occurred owing to a heat accumulation in the exothermic composition. The pad in Comparative Example 1 seems to have caused the low-temperature burns since the whole exothermic device was thick which resulted in overheating due to a heat accumulation in the exothermic composition, leading to great temperature variations of the exothermic device.

It is also understood that the water-containing reaction auxiliary layer formed between the exothermic reaction layer and integument acted as a heat buffer.

Further, the pad in Embodiment 3 was ultra-thin, and the exothermic composition was sandwiched between the films at the opposite surfaces. Consequently, the exothermic composition was not moved within the covering during use, or no movement occurred just before the end of exothermic action. With Comparative Example 1, the exothermic composition was found to be moved during use and just before the end of exothermic action.

The foregoing experiment shows that the pads according to the present invention assure a high degree of safety. These pads not only warm the human body to live comfortably in winter, but are highly promising to provide a therapeutic effect, based on its heating action, in treating symptoms involving local stiffness, pain, cold or the like.

Further, the ingredients may be dispersed uniformly since the exothermic reaction layer and reaction auxiliary layer are formed simply to have uniform thicknesses. The resulting products are highly reliable with respect to quality.

The pads according to the present invention are ultra-thin and soft, and therefore the exothermic device may be applied to an integument or clothing for excellent handling convenience.

In these embodiments, each pad has a peel-off sheet laminated thereon, and is inserted into a gas-tight outer pouch before being treated as a product.

In use, the outer pouch is broken to remove the pad, then the peel-off sheet is removed, and the pad is applied to a body surface or a garment such as underwear or a sock.

The foregoing relates to preferred exemplary embodiments of the invention, it being understood that other variants and embodiments thereof are possible within the spirit and scope of the invention, the latter being defined by the appended claims.

What is claimed is:

1. An exothermic device having an exothermic composition enclosed in a flat pouch formed of a film or sheet, at least one surface of said flat pouch being gas-permeable, said exothermic composition being made of a laminate, said laminate comprising an exothermic reaction layer comprising an exothermic substance as an essential ingredient thereof, and at least one reaction auxiliary layer comprising other ingredients, said exothermic reaction layer is stable in air and is activated to react with oxygen in the air by a reaction with said auxiliary layer.

2. An exothermic device as defined in claim 1, wherein the exothermic substance is a metal powder.

3. An exothermic device as defined in claim 1, wherein the exothermic reaction layer comprises a powder, and the reaction auxiliary layer comprises a liquid.

4. An exothermic device as defined in claim 3, wherein the layer of powder comprises at least one layer.

5. An exothermic device as defined in claim 4, wherein the liquid comprises water or an aqueous solution of a metallic chloride.

6. An exothermic device as defined in claim 1, wherein the exothermic reaction layer comprises a powder, and said reaction auxiliary layer consists of a plurality of layers, at least one of said plurality of layers comprising a liquid.

7. An exothermic device as defined in claim 1, wherein the exothermic reaction layer comprises a powder, and the reaction auxiliary layer comprises a mucous.

8. An exothermic device as defined in claim 7, wherein the layer of the powder comprises at least one layer.

9. An exothermic device as defined in claim 7, wherein the mucous comprises a mixture of a water retainer and water or a mixture of a water retainer, a metallic chloride and water.

10. An exothermic device as defined in claim 1, wherein the exothermic reaction layer comprises a powder, and said reaction auxiliary layer comprises a plurality of layers at least one of said plurality of layers comprising a mucous.

11. An exothermic device as defined in claim 1, wherein the exothermic reaction layer consists of a single layer of only a metal powder, and the reaction auxiliary layer comprises a layer of a mucous comprising a mixture of carbon powder, a water retainer, a metallic chloride and water, or a laminate consisting of a layer of a carbon powder and a layer of a mucous comprising a mixture of a water retainer, a metallic chloride and water whereby said exothermic reaction layer is stable in air and is activated to react with oxygen in the air by a reaction with said auxiliary layer.

12. An exothermic device as defined in claim 1, wherein the exothermic reaction layer consists of a single layer comprising a mixture of a metal powder and a carbon powder or two layers consisting of a layer of a metal powder and a layer of a carbon powder, and the reaction auxiliary layer consists of a layer of a mucous comprising a mixture of a water retainer, a metallic chloride and water.

13. An exothermic device as defined in claim 1, wherein the exothermic reaction layer consists of a single layer comprising a mixture of a metal powder and a water retainer or two layers consisting of a layer of a metal powder and a layer of a metallic chloride, and the reaction auxiliary layer consists of a layer of a mucous comprising a mixture of a carbon powder, a metallic chloride and water, or two layers consisting of a layer of a mucous comprising a water retainer and water a layer of a carbon powder laminated thereon.

14. An exothermic device as defined in claim 1, wherein the exothermic reaction layer consists of a single layer comprising a mixture of a metal powder and a part of a water retainer or two layers consisting of a layer of a metal powder and a layer of a part of a water retainer, and the reaction auxiliary layer consists of a layer of a mucous comprising a mixture of a carbon powder, the remainder of said water retainer, a metallic chloride and water.

15. An exothermic device as defined in claim 1, wherein the exothermic reaction layer consists of a single layer comprising a mixture of a metal powder, a carbon powder and water or three layers consisting of a layer of a metal powder, a layer of a carbon powder and a layer of a water retainer, and the reaction auxiliary layer consists of a layer comprising a liquid comprising a metallic chloride and water.

16. An exothermic device defined in claim 1, wherein the exothermic reaction layer is formed adjacent said surface of said pouch.

17. An exothermic device as defined in claim 1, wherein said reaction auxiliary layer comprises a mucous, and said film or sheet comprises a paper, a woven fabric, a nonwoven fabric or a gas-permeable foam sheet, said film or sheet being formed adjacent said mucous.

18. An exothermic device as defined in claim 17, wherein the paper, woven fabric, nonwoven fabric or gas-permeable foam sheet is thermally fusible.

19. An exothermic device as defined in claim 1, wherein said laminate comprises at least three layers including said exothermic reaction layer and said reaction auxiliary layer.

20. An exothermic device as defined in claim 19, wherein the exothermic reaction layer and the reaction auxiliary layer are laminated alternately.

21. An exothermic device as claimed in claim 1, further comprising a skin adhesive layer formed on one surface of said exothermic device, said exothermic device being formed as a pad.

22. An exothermic device as set forth in claim 21, wherein the skin adhesive layer comprises a compress layer or a pressure sensitive adhesive layer.

23. An exothermic device as set forth in claim 21, wherein the skin adhesive layer contains a skin absorbable medication.

24. An exothermic device having an exothermic composition enclosed in a flat pouch formed of a film or sheet, at least one surface thereof being gas-permeable, said exothermic composition comprises a laminate including an exothermic reaction layer having an exothermic substance as an essential ingredient thereof, and at least one reaction auxiliary layer including other ingredients, said laminate comprising at least two layers consisting of at least one of said exothermic reaction layer, and at least one of said reaction auxiliary layer, made in the order of a reaction auxiliary layer, an exothermic reaction layer, an exothermic reaction layer and a reaction auxiliary layer.

25. An exothermic device as defined in claim 24, in which an adhesive layer is formed on one surface of the exothermic device.

26. An exothermic device as defined in claim 24, wherein the exothermic reaction layer is partly formed on the reaction auxiliary layer.

27. An exothermic device as defined in claim 24, wherein a water retainer has been sprayed or laminated on said film or sheet and is used adjacent a layer of mucous.

28. An exothermic device having an exothermic composition enclosed in a flat pouch formed of a film or sheet, at least one surface thereof being gas-permeable, said exothermic composition comprises a laminate including an exothermic reaction layer having an exothermic substance as an essential ingredient thereof, and at least one reaction auxiliary layer including other ingredients, said exothermic device is formed as a pad comprising a skin adhesive layer formed on one surface, said skin adhesive layer comprises a compress layer or pressure sensitive adhesive layer, and a separate, skin absorbable medication-containing layer is formed on the skin adhesive layer.

29. An exothermic device as set forth in claim 28, wherein the separate, skin absorbable medication-containing layer is formed partly on a central portion of the skin adhesive layer or over the entire skin adhesive layer.

30. An exothermic device as set forth in claim 28, wherein the skin adhesive layer contains a water-absorptive polymer.

31. An exothermic device as set forth in claim 28, wherein at least one of the exothermic reaction layer, reaction auxiliary layer and skin adhesive layer contains a magnetic element and/or a far infrared radiator.

32. An exothermic device as set forth in claim 28, wherein the exothermic reaction layer is formed partly on the reaction auxiliary layer.

* * * * *